US006429012B1

(12) United States Patent
Kraus et al.

(10) Patent No.: US 6,429,012 B1
(45) Date of Patent: Aug. 6, 2002

(54) CELL POPULATION CONTAINING NON-FETAL HEMANGIOBLASTS AND METHOD FOR PRODUCING SAME

(75) Inventors: Morey Kraus; Paul Wilder, both of Worcester, MA (US)

(73) Assignee: Viacell, Inc., Worcester, MA (US)

( * ) Notice: Subject to any disclaimer, the term of this patent is extended or adjusted under 35 U.S.C. 154(b) by 0 days.

(21) Appl. No.: 09/591,198

(22) Filed: Jun. 9, 2000

Related U.S. Application Data

(63) Continuation of application No. 09/138,928, filed on Aug. 24, 1998, now abandoned, which is a continuation-in-part of application No. 08/944,755, filed on Oct. 6, 1997, now Pat. No. 5,925,567.

(51) Int. Cl.$^7$ ................................................. C12N 5/02
(52) U.S. Cl. ........................ 435/372; 435/374; 435/372; 435/371; 435/395
(58) Field of Search .............................. 435/2, 7.24, 30, 435/343, 372, 240.2, 374, 371, 395, 402, 403; 424/93.1, 93.7

(56) References Cited

U.S. PATENT DOCUMENTS

| 5,635,387 A | 6/1997 | Fei et al. ..................... 435/378 |
| 5,744,347 A | 4/1998 | Wagner et al. ............ 435/240.2 |
| 5,874,301 A * | 2/1999 | Keller et al. |
| 5,925,567 A * | 7/1999 | Kraus et al. |
| 6,060,052 A * | 5/2000 | Murray et al. |

FOREIGN PATENT DOCUMENTS

| WO | WO 91/16116 | 10/1991 |
| WO | WO 93/08268 | 4/1993 |

OTHER PUBLICATIONS

Nishikawa, S., "Embryonic stem cells as a source of hemtopoirtic and vascular endothelial cells in vitro" Journal Allergy Clin Immunol, Dec. 1997, 100:S102–S104.*
Fujisaki et al. Blood, vol. 94, pp. 1926–1932.
B.Q. shi et al., "Evidence for Circulating Bone Marrow-–Derived Endothelial Cells", Blood, vol. 92, No. 2, 1998, pp. 362–367, XP002125750, the whole document.
A.G. Elefanty et al., "Hematopoietic Specific Genes are Not Induced During In Vitro Differentiation of scl–null Embryonic Stem Cells", Blood, vol. 90, No. 4, 1997, pp. 1435–1447, XP002125751, the whole document.

M. Tavassoli, "Embryonic and Fetal Hemopoeiesis: An Overview", Blood Cells, vol. 17, No. 2, 1991, pp. 269–281, XP002125752, the whole document.
R. Auerbach et al., "Hematopoeietic Stemm Cells in the Mouse Embryonic Yolk Sac", Stem Cells, vol. 14, 1996, pp. 269–280, XP002125753, the whole document.
L. Robb et al., "The hemangioblast–An Elusive Cell Captured in Culture" Bioessays, vol. 20, 1998, pp. 611–614, XP002125754, the whole document.
K. Choi et al., "A Common Precusor for Hematopoietic and Endothelial Cells", Development, vol. 125, 1998, pp. 725–732, XP002125755, the whole document.
A. Eichmann et al., "Ligand–Dependent Development of the Endothelial and Hemopoietic Lineages From Embryonic Mesodermal Cells Expressing Vascular Enthelial Growth Factor Receptor 2", PNAS, vol. 94, 1997, pp. 5141–5146, XP002125756, the whole document.
"A newly Discovered Class of Human Hematopoietic Cells with SCID–Repopulating Activity", Bhatia et al., Nature Medicine, vol. 4, No. 9, 9/98, pp. 1038–1045.
"Dye Efflux Studies Suggest That Hematopoietic Stem Cells Expressing Low or Undetectable Levels of CD34 Antigen Exist in Multiple Species", Goodell et al., Nature Medicine, vol. 3, No. 12, 12/97, pp. 1337–1345.
"A Common Precursor for Hematopoietic and Endothelial Cells", Choi et al., published Jan. 22, 1998, pp. 725–732.
"Human Bone Marrow CD34$^-$ Cells Engraft In Vivo and Undergo Multilineage Expression That Includes Giving Rise to CD34$^+$ Cells", Zanjani et al., 1998 International Society for Experimental Hematology, Feb. 5, 1998, pp. 24–31.
"Ex Vivo Expansion of Cord Blood–Derived Stem Cells and Progenitors"; Malcolm A.S. Moore and Iffath Hoskins; Blood Cells; Springer–Verlag, New York Inc. 1994; Blood Cells (1994) 20:468–481.

* cited by examiner

Primary Examiner—Leon B. Lankford, Jr.
Assistant Examiner—Ruth A. Davis
(74) Attorney, Agent, or Firm—Fish & Richardson, P.C.

(57) ABSTRACT

Methods are provided for expanding populations of non-fetal hemangioblasts, for example a method including (a) providing a first cell population containing non-fetal hemangioblasts; and (b) growing the enriched cell culture under conditions that promote the proliferation of the non-fetal hemangioblasts. Preferred populations include non-fetal uncommitted human hemangioblasts.

25 Claims, 10 Drawing Sheets

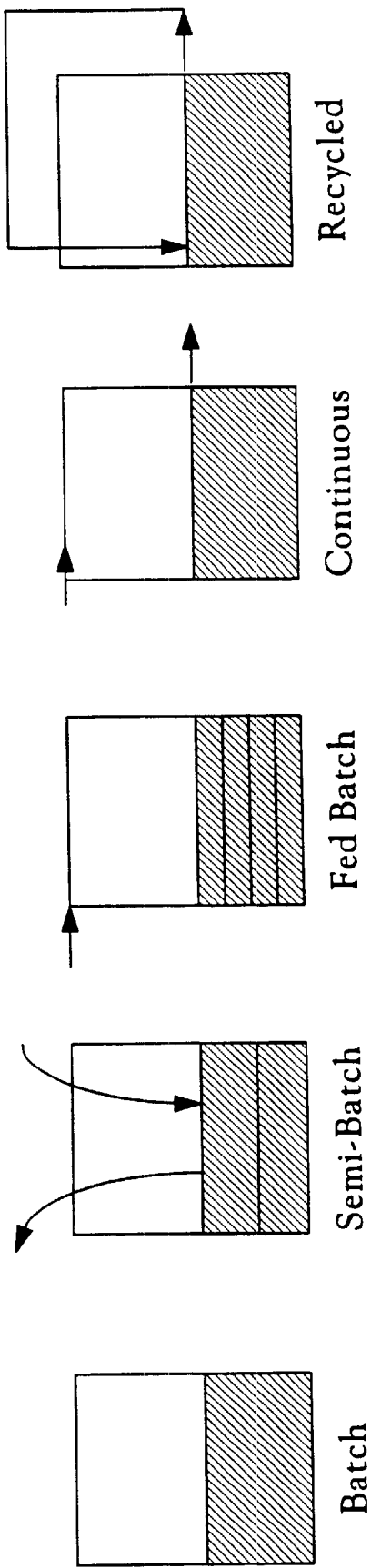

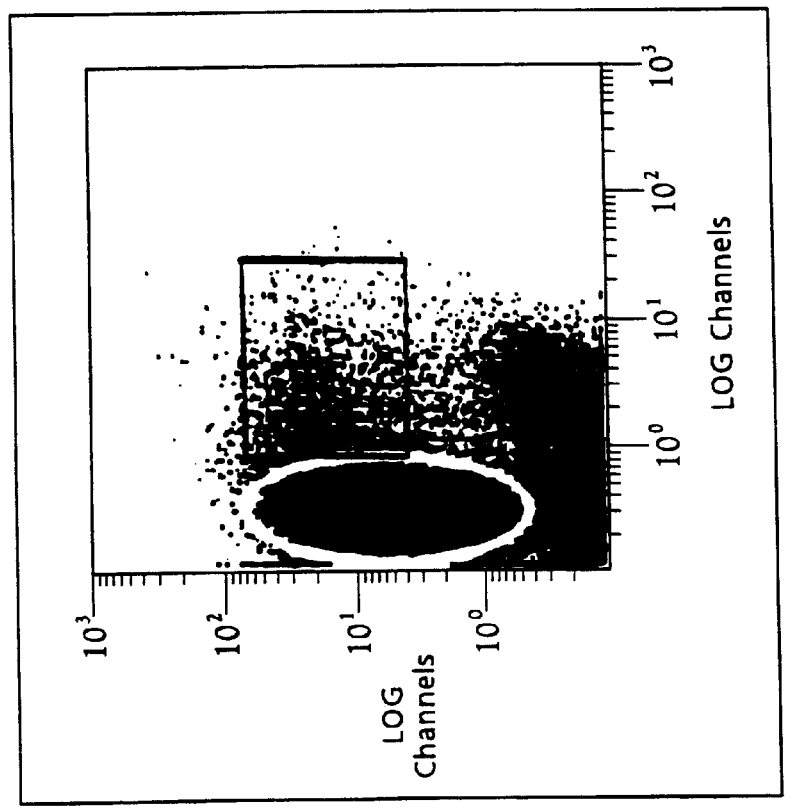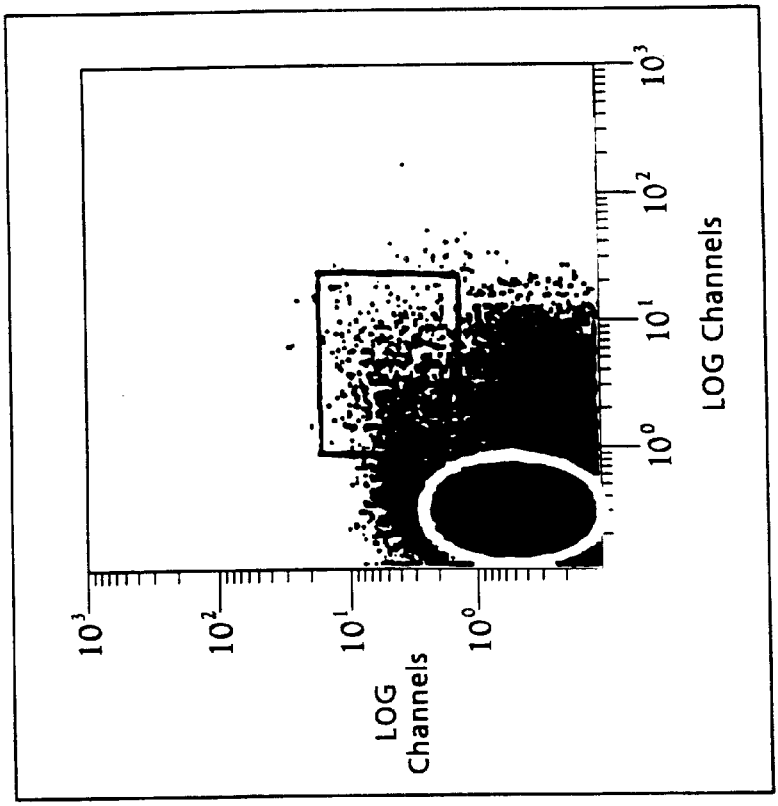
Week 3 of Selective Culture
FIG. 9

CELL POPULATION CONTAINING NON-FETAL HEMANGIOBLASTS AND METHOD FOR PRODUCING SAME

RELATED APPLICATIONS

This application claims priority under 35 USC §120 of U.S. application Ser. Nos. 09/138,928 and 08/944,755, the entire disclosures of which are hereby incorporated herein by reference. This application is a continuation of U.S. Ser. No. 09/138,928, which was filed Aug. 24, 1998 and abandoned effective Jun. 10, 2000, and is a continuation-in-part of U.S. application Ser. No. 08/944,755, which was filed Oct. 6, 1997 and which issued Jul. 20, 1999 as U.S. Pat. No. 5,925,567.

BACKGROUND OF THE INVENTION

The invention relates to cell populations and methods of producing them.

There is strong empirical evidence that during murine embryogenesis a common precursor to hematopoietic and endothelial cells exists. A pluripotent precursor cell, caled the hemangioblast, which carries this bipotential, was first hypothesized in 1900 by W. His. Putative hemangioblasts have been teased out of embryonic cultures and manipulated by cytokines to differentiate along either hematopoietic or endothelial pathways. Using population kinetics it has been demonstrated that pre-endothelial/pre-hematopoietic cells in the embryo clearly arise out of a phenotype CD 34– population. (Choi et al., A Common Precursor for Hematopoietic and Endothelial Cells, Development 125, 725–732 (1998).)

Additionally, it has recently been found that sheep can be successfully engrafied in utero with adult human CD34–, Lin– cells, resulting in long-term engraftment and multilineage hematopoietic cell/progenitor expression. Significant numbers of human CD34+ cells were detected in the animals that were transplanted with the CD34–, Lin– cells. The resulting conclusion was that the CD34– fraction of normal human bone marrow contains cells capable of enabling in utero engraftment, possibly through the differentiative production of engraftable CD34+ cells in the fetal microenvironment. (Zanjani et al., Human Bone Marrow CD34– Cells Engraft In Vivo and Undergo Multilineage Expression That Includes Giving Rise to CD34+ Cells, Experimental Hematology 26:1–221 (1998).)

SUMMARY OF THE INVENTION

The invention provides enriched stem cell containing populations that can be expanded, and thus can be of great value to patients in need of cellular therapy, e.g., cancer therapy, immunotherapy, and gene therapy.

Preferred populations include at least 5% human non-fetal uncommitted hemangioblasts, i.e., common precursors of hematopoietic cells and endothelial cells; by "uncommitted" it is meant that the hemangioblasts are not yet committed to either lineage, i.e., under the proper conditions the cells can become either hematopoietic cells or endothelial cells. These hemangioblasts are stable, not transient, and are present in the tissue of fully developed individuals, such as in newborn infants and adults. We have, in fact, discovered that these hemangioblasts can be isolated from cord blood following birth. The presence of hemangioblasts in non-embroid tissue was unexpected and presents novel opportunities.

As shown schematically in FIG. 1, the uncommitted hemangioblasts can be stimulated to become hematopoietic cells or endothelial cells, by selecting appropriate growth factors in which to expand the population, as will be discussed in detail below. Thus, when supplied with one cocktail of growth factors, these hemangioblasts can be amplified (i.e., the number of hemangioblasts can be increased), and/or they can be differentiated to provide a supply of hematopoietic cells, for example to patients who are immune compromised or require gene therapy with hematopoietic cells. When supplied with a different cocktail, the hemangioblasts can be amplified and/or can be differentiated to become endothelial cells, useful for example in wound healing, e.g., healing of slow or non-healing diabetic sores. The endothelial cells can also be transfected ex vivo, e.g., with genes which produce angiogenic factors, and used in gene therapy, for example to stimulate angiogenesis in patients with vascular or cardiac insufficiency. Recent studies have demonstrated the feasibility of cytokine gene transfer to enhance the antitumor activities of host immune cells. Endothelial cells forming the vascular supply of tumors may be useful vehicles for the delivery of cytokine molecules in order to effect tumor immunotherapy. Ojeifo, et al., Cytokines Mol Ther 1996 Jun;2(2):89–101.

Populations which have been expanded to contain a significant percentage of these uncommitted hemangioblasts will provide a high level of engraftment while starting from a relatively small sample, since the uncommitted hemangioblasts can be stimulated to become hematopoietic cells by supplying them with appropriate growth factors.

Accordingly, in one aspect, the invention features a method for providing a cell population containing non-fetal hemangioblasts. The method includes (a) providing a first cell population containing non-fetal hemangioblasts; and (b) growing the first cell population under conditions that promote the proliferation of the non-fetal hemangioblasts. The invention also features cell populations formed by expansion of a population containing non-fetal hemangioblasts.

Preferred embodiments of the invention include one or more of the following features. In the growing step (step (b), above), the conditions are such that the number of said non-fetal hemangioblasts and their proximity to each other are sufficient to increase the proportion of non-fetal hemangioblasts in the population. The method includes, prior to the growing step, enriching the first cell population for non-fetal hemangioblasts. The method also includes separating the non-fetal hemangioblasts from other cells in the cell culture, e.g., by a negative selection process. The separating step is performed concurrently with, intermittently during, or following, the growing step. The separating step is performed more than once during cell proliferation, e.g., every 5 to 10 days. The growing step includes providing at least one growth factor, more preferably a cocktail of growth factors, to the cell population during cell proliferation. At least some of the non-fetal hemangioblasts, preferably at least 2%, more preferably at least 5%, more preferably at least 15% and most preferably at least 25%, are uncommitted human hemangioblasts. At least some of the non-fetal hemangioblasts, preferably at least 2%, more preferably at least 5%, more preferably at least 15% and most preferably at least 25%, are CD 34–, Lin– cells. The percentage of cells that are CD 34–, Lin– and/or are uncommitted human hemangioblasts is higher in the enriched cell culture than in the starting cell culture. The uncommitted human hemangioblasts are characterized as: CD2–, CD3–, CD 14–, CD16–, CD19–, CD24–, CD56–, CD66b–, glycophorin A–. The uncommitted human hemangioblasts are further characterized as: flk-1+, CD45+, CXCR4+, MDR+ (Pgp).

In another aspect, the invention features an enriched cell population comprising non-fetal hemangioblasts, the enriched cell population resulting from expansion of a starting cell population containing fewer non-fetal hemangioblasts than the enriched cell population.

Preferred embodiments include one or more of the following features. The starting cell population contains at least 10% fewer non-fetal hemangioblasts than the enriched cell population. The percentage of cells that are non-fetal hemangioblasts in the enriched cell culture is the same as or higher than the percentage of cells that are non-fetal hemangioblasts in the starting cell culture.

The invention also features a composition of cells in which at least 2%, more preferably at least 5%, more preferably at least 15%, and most preferably at least 25% of the cells are non-fetal hemangioblasts, and methods of making such a composition. Preferably the non-fetal hemangioblasts are human uncommitted hemangioblasts that are Lin– cells and are characterized as: CD2–, CD3–, CD14–, CD16–, CD19–, CD24–, CD56–, CD66 b–, glycophorin A–, flk-1+, CD45+, CXCR4+, MDR+.

Other features and advantages of the invention will be apparent from the following detailed description, the drawings, and the claims.

BRIEF DESCRIPTION OF THE DRAWINGS

FIGS. 3–3d are schematic diagrams of alternative modes of operation of systems according to different embodiments of the invention.

FIG. 9 is a group of dot plots showing the population profile of reselected cells at week three of selective culture using CXCR4 vs. Flk-1 and Pgp (MDR) vs. Flk-1.

DESCRIPTION OF THE PREFERRED EMBODIMENTS

As discussed above, the invention broadly features a method of enriching the precursor cell content of a population containing non-fetal hemangioblasts (hereafter referred to as "target cells"). Preferably the cells are CD 34–, Lin– cells or uncommitted hemangioblasts that are characterized as: CD2–, CD3–, CD14–, CD16–, CD19–, CD24–, CD56–, CD66b–, glycophorin A–, flk-1+, CD45+, CXCR4+, MDR+.

Selection

Preferred methods of expanding and enriching the population include selecting target cells from non-target cells in the cell population, concurrently with proliferation, intermittently during proliferation or following proliferation. Cell proliferation and cell selection can be carried out using an almost infinite variety of different techniques and settings, of which only a few are described below by way of example. Many other techniques will be readily perceived by those skilled in the art, for example selection by flow cytometry, and selection by using chemical agents to kill unwanted cells.

The preferred selection methods used in the invention can broadly be classed as positive selection (providing a selection element having an affinity for, i.e., Aselecting@, target cells) and negative selection (providing a selection element having an affinity for, i.e., Aselecting@, non-target cells). These two selection techniques, used alone or in combination, allow unwanted cells to be removed from the system and target cells to be harvested whenever desired.

Figure 1:
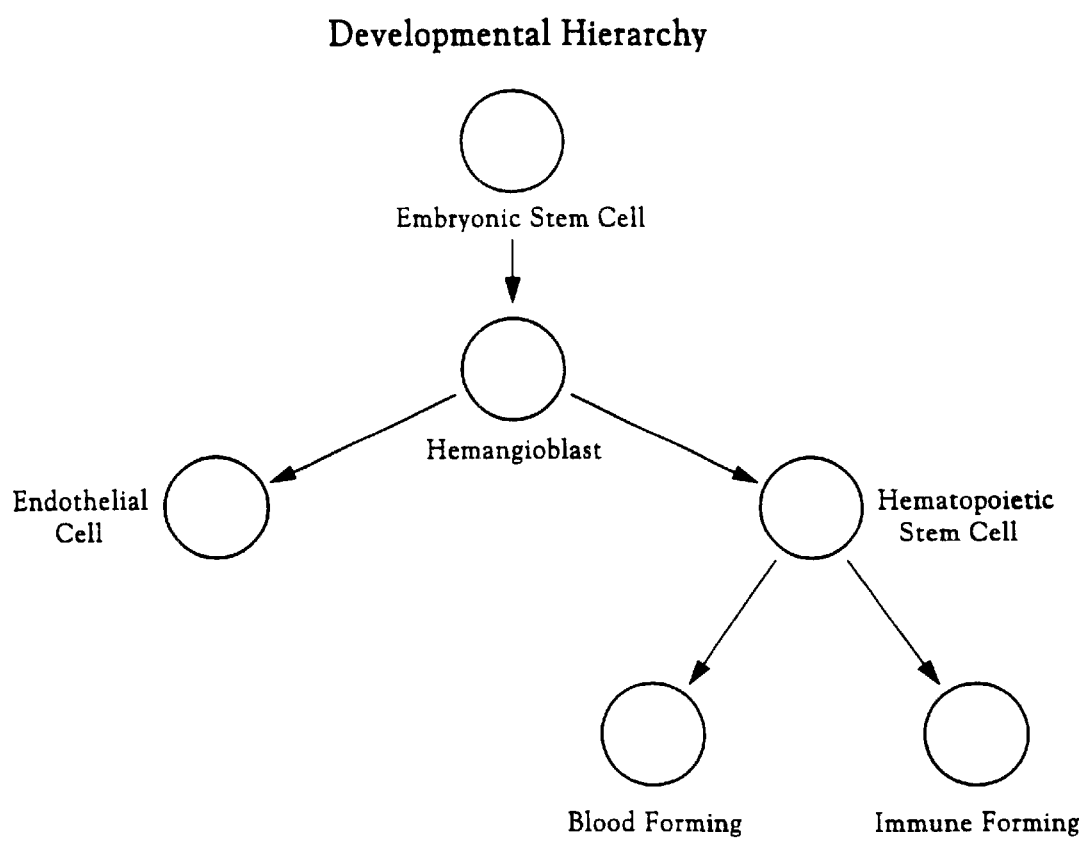
FIG. 1 is a schematic diagram illustrating that hemangioblasts are the common precursor of hematopoietic and endothelial cells.
Figure 2:
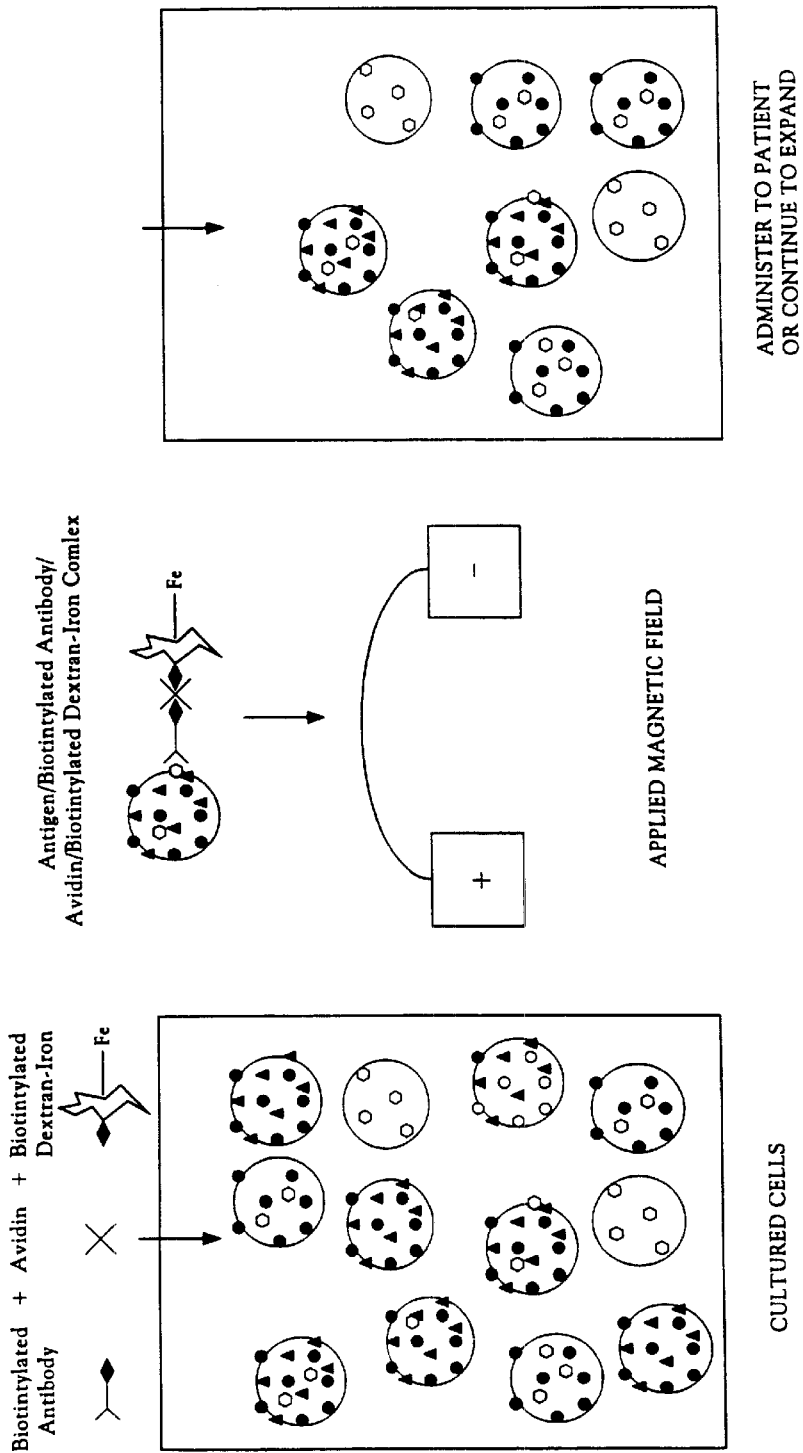
FIG. 2 is a highly enlarged diagrammatic view of a system for positive selection of a target cell (a hemangioblast).

An example of a positive selection technique is illustrated diagrammatically in FIG. 2. Briefly, one or more anti-dextran conjugated antibodies specific for the predetermined target population is introduced into the culture. After a specified incubation time, a magnetic dextran iron particle colloid is introduced into the cell suspension. A Cell/Antigen/Antibody/Anti-dextran/Dextran/Iron Complex forms. This complex is then passed through a magnetic field. Positively selected cells remain in the magnetic field while cells which do not have the iron conjugated complex are removed. After capture and rinsing the magnetic field is removed and the positively selected predetermined target population is returned to the nutrient medium.

Figure 2A:
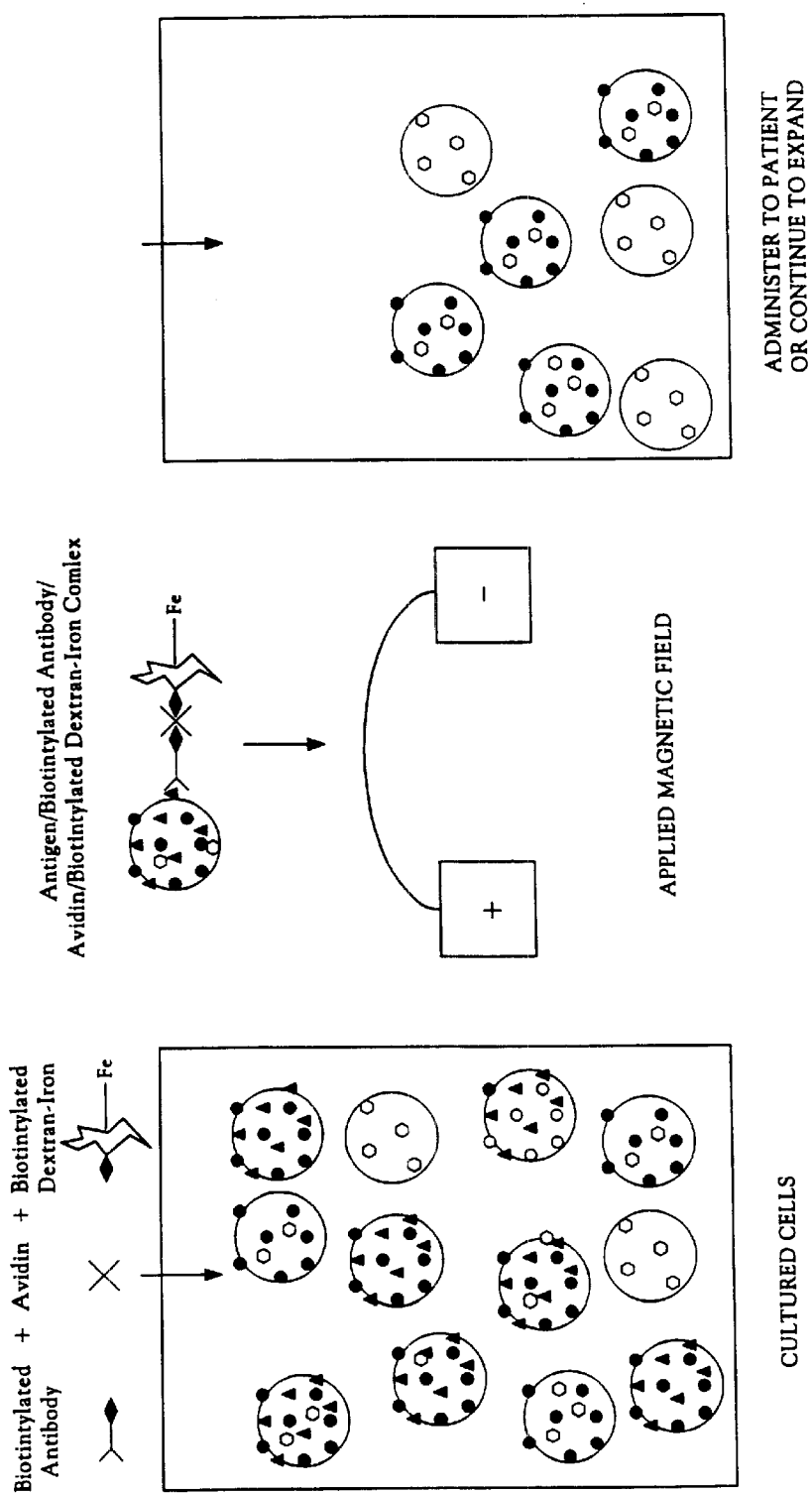
FIG. 2a is a highly enlarged diagrammatic view of a system for negative selection of a non-target cell (a non-hemangioblast).

An example of a negative selection technique is illustrated diagrammatically in FIG. 2A. Briefly, one or more anti-dextran conjugated antibodies specific for a predetermined population which is not of the predetermined target population is introduced into the culture. After a specified incubation time, a magnetic dextran iron particle colloid is introduced into the cell suspension. A Cell/Antigen/Antibody/Antidextran/Dextran/Iron Complex forms. This complex is then passed through a magnetic field, removing cells not of the predetermined target population from the nutrient medium. The predetermined target population is collected downstream and returned to the nutrient medium.

Clearly, many other techniques can be utilized for both positive and negative selection, as long as the desired affinity is provided by the selection element.

The selection element can include other components in addition to the antibody molecules that are used to perform the selection (the "selection molecules"), e.g., a solid support to which the selection molecule is bound. The solid support can be formed of a material that will aid in performing the selection or in maintaining the selection molecules in a desired position or introducing and removing them from the system. For example, as described above with reference to FIG. 2, the selection molecule can be bound to iron or other magnetic particles to allow the selected cells to be easily removed from the system by application of a magnetic field and then collected by removal of the magnetic field. Alternatively, the selection molecules can be bound onto the wall of a vessel containing the nutrient medium, or of a chamber through which the nutrient medium flows during the method. Glass or other inert, impermeable beads can also be used as a solid support. If beads or other particles are used, they can be provided in a packed configuration, through which the nutrient medium flows, or can be introduced into the system in a loose form, suspension, or in any desired type of array. As will be readily understood, a wide variety of other solid supports can be used.

As shown in FIGS. 3–3D, the selection element can be used in a variety of modes of operation in which nutrient media is supplied to and removed from the system in different manners. These modes of operation range from a selective batch culture (FIG. 3), in which nutrient media is supplied at the beginning of cell proliferation and is neither added to nor removed, to continuous flow or recycled flow cultures (FIGS. 3C and 3D, respectively) in which either fresh or recycled nutrient media flows through the system substantially continuously. These alternative modes will be discussed in detail below.

In a selective batch culture (FIG. 3), a nutrient medium is introduced into a vessel, and a starting sample of cells is also introduced into the vessel. During cell proliferation, nutrient medium may or may not be exchanged. However, selected cells are physically selected, i.e., separated from other cells in the nutrient medium by binding to a selection element, either continuously, intermittently or following cell proliferation. These selected cells may be cells of a target population, if positive selection is used, or unwanted cells, if negative selection is used. Dual (positive and negative) selection can be accomplished by providing positive selection molecules on the surface of the vessel, beads, baffles, impellers, etc. while removing unwanted cells by negative selection. Alternatively, cells may be positively or negatively selected outside of the culture vessel and then returned.

The selective semi-batch (3A) and selective fed batch (3B) modes of operation are similar to the selective batch mode with regard to positive and negative selection. The significant difference between these three modes is in the treatment of the nutrient medium. While in the batch mode the volume of the medium remains constant and the medium is not refreshed (it may be supplemented), the semi-batch mode allows for a partial refreshment of spent medium with new medium and the fed batch mode allows for an incremental increase in the medium volume over time.

Cell growth and selection can also be performed in a continuous (FIG. 3C) or recycling (FIG. 3D) mode of operation. In these two modes, the system includes a chamber having an inlet and an outlet, and nutrient media is caused to flow through the chamber from the inlet to the outlet. In continuous mode, new nutrient media flows through the chamber from a source or reservoir, while in recycling mode the same nutrient media is cycled through the chamber repeatedly. If desired, a system can be configured to be run alternatively in either continuous or recycling mode. Any desired selection element can be used in these modes of operation.

Process Parameters

A number of parameters can be varied to affect the rate and purity of the cell output obtained during cell proliferation.

For example, the concentration, type and combination of growth factors can be varied to acheive a desired result. Suitable growth factors for promoting cell proliferation include Stem Cell Factor (SCF; R&D Systems Catalog No. 255-SC-010), Thrombopoietin (TPo; R&D Systems Catalog No. 288-TP-005) and FLT3 (R&D Systems Catalog Nos. 308-FK-005 and 308-FK-025), all of which are commercially available from R&D Systems, Inc., 614 McKinley Place Nebr., Minneapolis, Minn. 55413. Preferably at least 10 ng/ml of each of these growth factors is added, more preferably 10–500 ng/ml. If the cell population contains uncommitted hemangioblasts, the growth factors supplied will determine whether the hemangioblasts become hematopoietic cells or endothelial cells. To obtain hematopoetic cells, the hemangioblasts can be supplied with a cocktail containing SCF, TPo and FLT3; to obtain endothelial cells the hemangioblasts can be supplied with a cocktail containing VEGF. Suitable concentrations of SCF, TPo and FLT3 are given above. Suitable concentrations of VEGF are from 5 to 100 ng/ml.

We have also discovered that proliferation of stem cells is influenced by the proximity of the cells to each other in the culture. We found that proliferation of the target cells is enhanced by periodically increasing the relative concentration of the target cells in the culture during proliferation. The concentration can be increased, for example, by separating out non-target cells and then placing the remaining target cells in closer proximity to each other, e.g., by decreasing the cross-sectional diameter of the culture vessel.

If separation is performed, as discussed above, the duration of the time periods between separations will affect cell proliferation. The removal of non-target cells from the culture promotes cell proliferation by reducing build-up of by-products and inhibitors, and thus frequent selection will result in enhanced proliferation of the target population. In most cases, it is preferred that the selection remove substantially all of the non-target cells, as this will minimize inhibition. However, in some cases it may be desirable to allow other populations to proliferate with the target population. Moreover, selection can be eliminated completely if a mixed population can be used or would be desirable in the intended application, e.g., bone marrow restoration where a Graft vs. Leukemia (GVL) type effect is desired.

Other factors that will influence the composition of the cell population resulting from proliferation include the nutrient media used, the gas tension in the incubator, the seeding density (initial concentration of non-fetal hemangioblasts), and stirring of the culture. These factors could be readily adjusted by one skilled in the art to obtain a desired result.

Therapeutic Use

Figure 4:
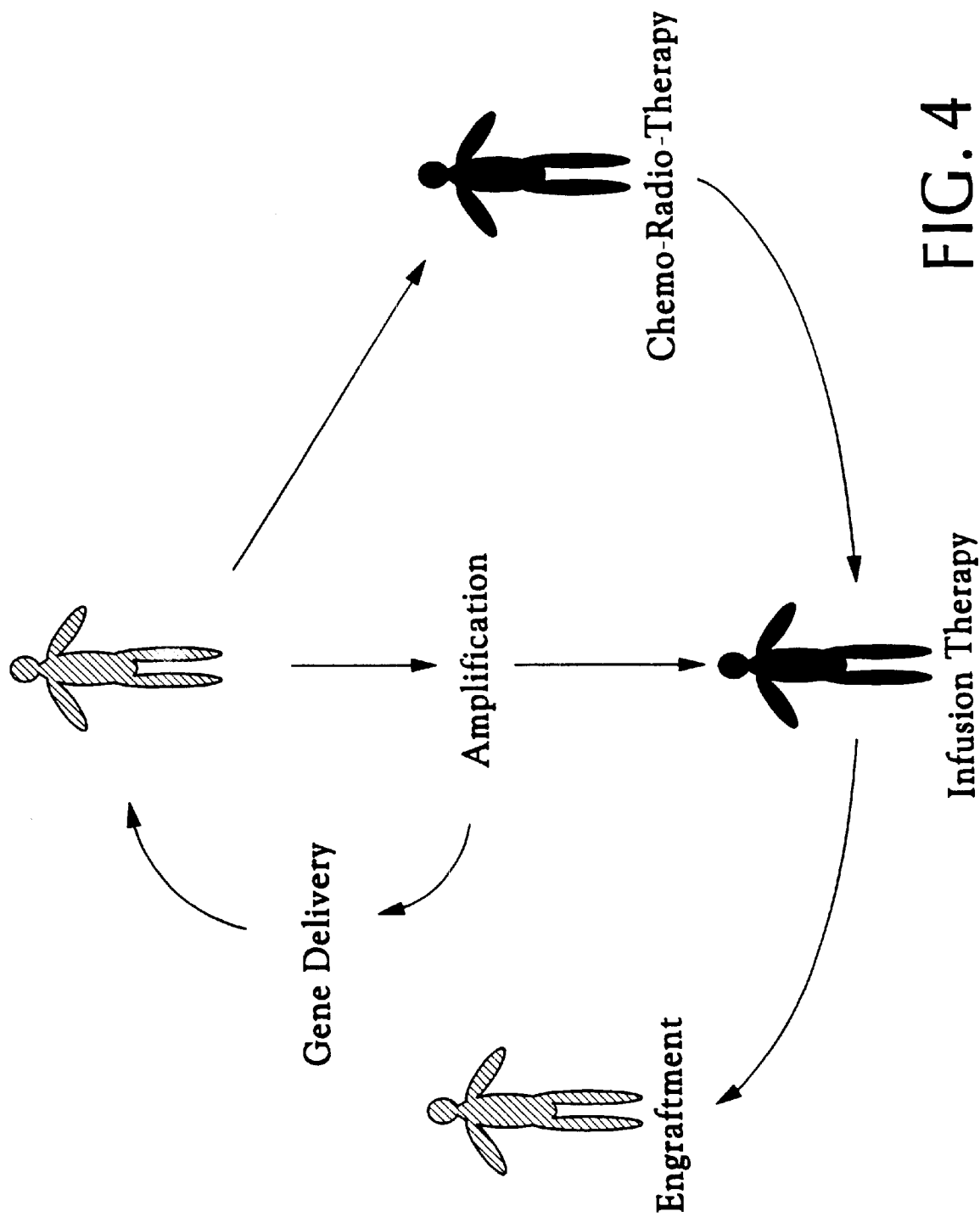
FIG. 4 is a schematic flowchart showing a method, according to one embodiment of the invention, of treating a patient with hematopoietic stem cells.

As shown schematically in FIG. 4, a patient requiring immunotherapy has a small volume of blood drawn. This blood is then used as described above to produce a pool of autologous or allogeneic non-fetal hemangioblasts, which is administered, using standard methods, to the patient as an immune system booster prior to a treatment damaging the patient=s immune system and/or blood forming system (e.g., chemotherapy), and/or as a stimulant to the patient=s compromised immune or blood forming system after the treatment. Cells are administered to reconstitute portions of the immune system, e.g., bone marrow, using methods described in the literature, e.g., in U.S. Pat. Nos. 5,130,144, 5,635,386, 5,670,147, 5,646,043, 5,635,387 and 5,061,620, the disclosures of which are incorporated herein by reference.

Alternatively, a cell sample can be used to produce a pool of a selected population of cells, by first forming a population of non-fetal hemangioblasts and then placing the cells in a culture under conditions selected to promote the proliferation of a desired population of cells using the non-fetal hemangioblasts as precursors.

Newly formed endothelial cells differentiated from the hemangioblasts can be used in various cell therapies. For example, the cells can be used in wound healing, e.g., donor endothelial cells delivered by injection have been found to localize exclusively to neovascular zones of recipient mice. T. Asahara et al., Isolation of Putative Progenitor Endothelial Cells for Angiogenesis, Science, Vol. 275, p. 964, Feb. 14, 1997. Endothelial cells can also be used in gene therapy, for example endothelial cells can be delivered to inhibit vascularization of tumors, e.g., using switchable genes encoding angiogenesisinhibiting proteins as disclosed in U.S. Pat. Nos. 5,733,876, 5,712,291 and 5,698,586, the disclosures of which are incorporated herein by reference. An in vitro production system would be particularly useful for angiogenic activity assays used in cancer detection, screening of anti-angiogenesis agents for cancer therapeutics, and for graft tissue engineering applications, e.g., grafts for neovascularization in the treatment of eschemic cardiovascular diseases, including coronary artery, peripheral artery and cerebral vascular.

EXAMPLE 1

Growth Medium: Iscove=s Modified Dulbecco=s Medium (1MDM)(100 ml), Pen/Strep (50 1l), BSA (50 mg/ml), Insulin (50 1g/ml), Transferrin (1 mg/ml), Low Density Lipoprotein (100 1l), 2-Mercapto-Ethanol (7 1l of 1/100 solution), FLT3 (100 ng/ml), SCF (100 ng/ml), Tpo (100 ng/ml).

1. Obtained an Umbilical Cord Blood extract containing Lin– cells, including CD 34–, Lin– cells.
2. Separated the Mononuclear Fraction (MNF) by Ficoll Density Gradient Centrifugation.
3. Separated Lin– cells from the MNF using negative selection.
4. Inoculated a culture plate containing 10 ml of the above growth medium with 5,000 Lin– cells/ml, using the cells from step 3.
5. Placed the culture plate in an incubator at 37EC and 5% CO2.
6. On day 7, harvested the culture and purified by negative (–) selection, as described below, for Lin– cells.
7. Inoculated fresh growth medium with the Lin– cells obtained in step 6, at a concentration of 5,000 cells/ml, and placed the culture plate in an incubator at 37EC and 5% CO2.
8. Multiple cycles of reselection, using the specified medium for interim growth, were performed on days 7, 14 and 21.

Negative (–) Selective Procedure (Step 6 above):

We incubated the cells in the culture with a cocktail containing selection molecules (antibodies to surface antigens) linked to an anti-dextran molecule. After incubation, a magnetic dextran iron particle colloid was introduced into the cell suspension. A Cell/Antigen/Antibody/Anti-dextran/Dextran/Iron Complex formed. This complex was then passed through a magnetic field, removing cells not of the predetermined target population from the nutrient medium. The target population was collected downstream and returned to the nutrient medium. The detailed procedure we followed is described below.

1. A sample of human cord blood was obtained.
2. A Mononuclear Cell Composition (Buffy Coat) using Ficoll-Paque (Pharmacia Biotech) Gradient Centrifugation was prepared and rinsed twice with PBS (without Ca++ or Mg++).
3. 100 1l of antibody cocktail containing bispecific Tetrameric Antibody Complex: Anti-Dextran/Anti-CD3, CD2, CD56, CD24, CD19, CD66b, CD14, CD16 and Glycophoran A (StemSep) was added to 1 ml containing 2×107 Mononuclear Cells obtained in Step 2 above.
4. This mixture was then incubated for 15 minutes at room temperature.
5. 60 1l of colloidal magnetic dextran iron particles (StemSep) was added.
6. This mixture was incubated for 15 minutes at room temperature.
7. During the incubation steps above, a 0.6" diameter separation column (StemSep), pump (Cole-Parmer), and magnet (StemSep) were assembled and the flow rate calibrated according to the column manufacturer's specifications.
8. Once the column was in place within the magnetic field and fully primed with PBS (without FBS) the sample was loaded into the top of the column.
9. The pump was started in the downward direction to allow the sample to run into the matrix of the column.
10. PBS plus FBS was added to the top of the column intermittently so as not to allow the sample front to enter the column matrix until 25 mls were collected downstream of the magnet.
11. The 25 ml sample containing the target population was centrifuged at 800 RPM for 15 minutes.
12. The resulting pellet was resuspended in 1 ml of HBS and transferred to a 1.5 ml eppendorf tube.
13. The sample was rinsed twice with repeated centrifugation at 800 RPM and resuspended in 1 ml HBS.
14. Following analysis by flow cytometry the target cells were plated in the growth medium at a concentration of 1000 cells/ml.

Data obtained from the cultures described above is shown in FIGS. 5–9.

Figure 5:
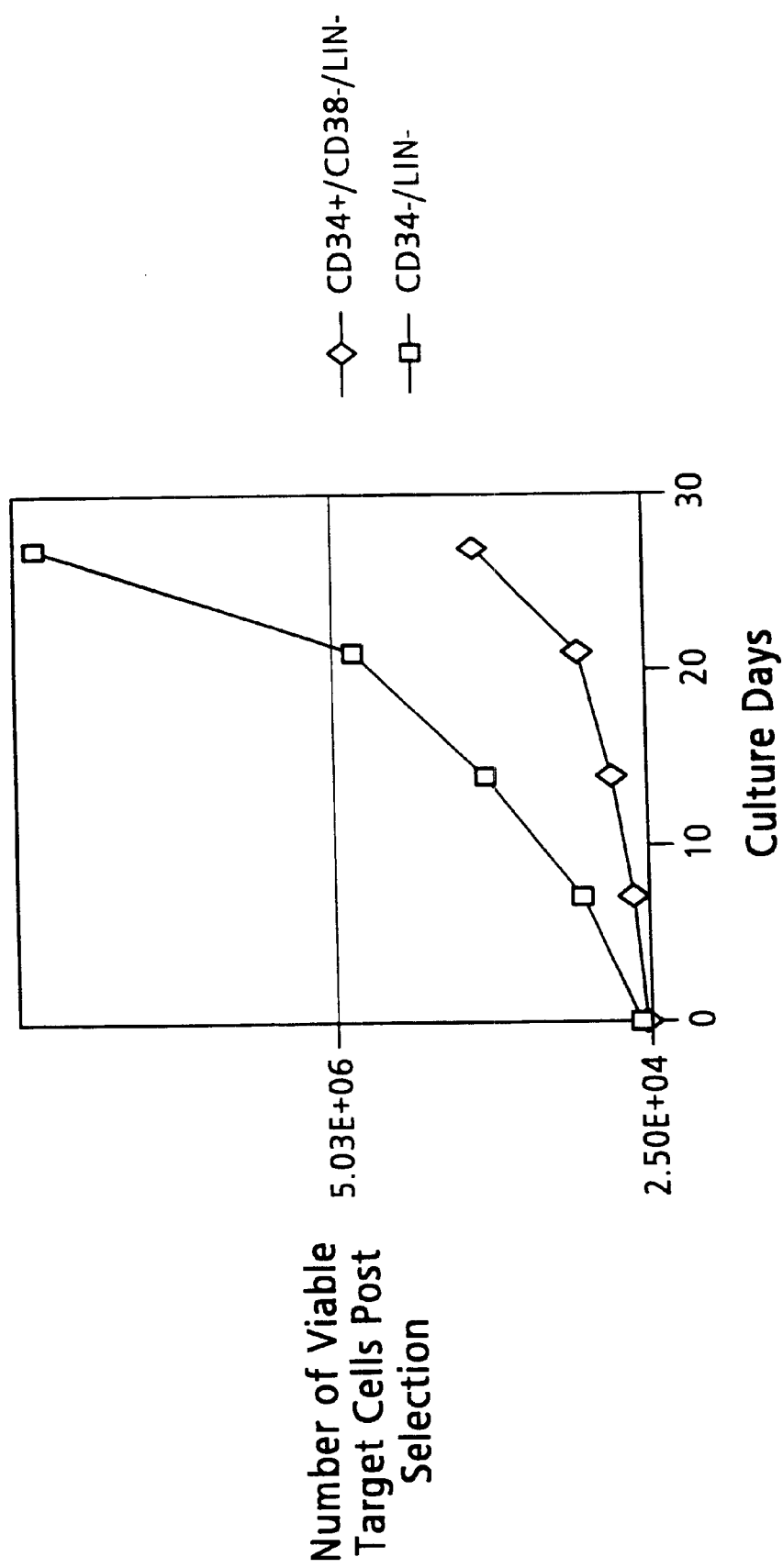
FIG. 5 is a graph showing the growth kinetics of CD34+/CD38–/Lin– and CD34–/CD38–/Lin– target cells over a 30 day culture period.

FIG. 5 is a graph showing the growth kinetics of CD34+/CD38–/Lin– and CD34–/CD38–/Lin– target cells over a 30 day culture period. As shown in FIG. 5, the population of CD34–, Lin– cells continued to expanded throughout the 30 day period.

Figure 6:
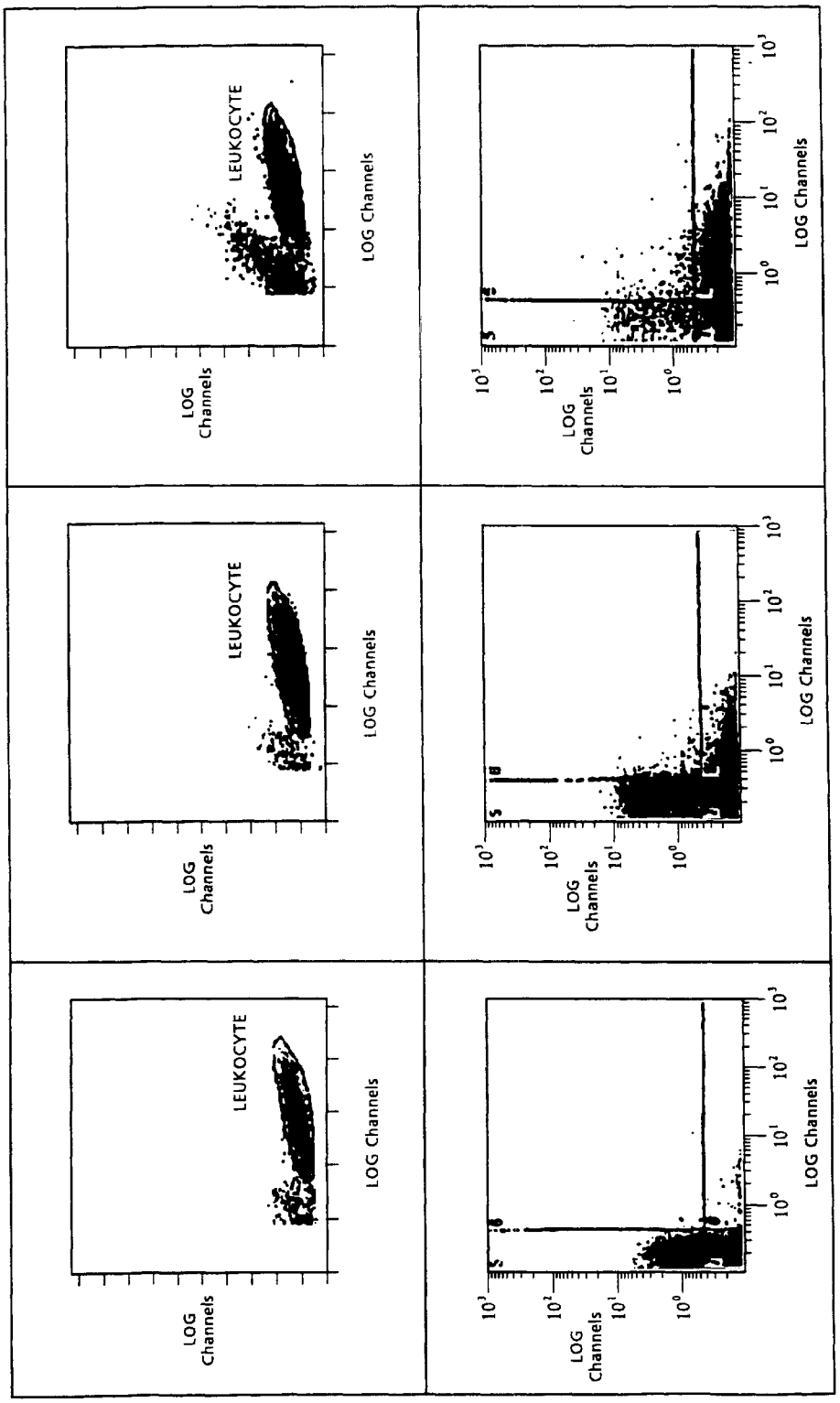
FIG. 6 is a group of dot plots showing the population profile of reselected cells prior to subsequent reselection using CD34 vs. Lineage (Lin) markers over a three week period.

FIG. 6 is a group of dot plots showing the population profile of reselected cells prior to subsequent reselection using CD34 vs. Lineage (Lin) markers over a three week period. We observed (a) continual output of lineage positive progeny prior to each selection step; (b) continual amplification of CD34+, Lin– cells, and (c) continual amplification of CD34–, Lin– cells.

Figure 7:
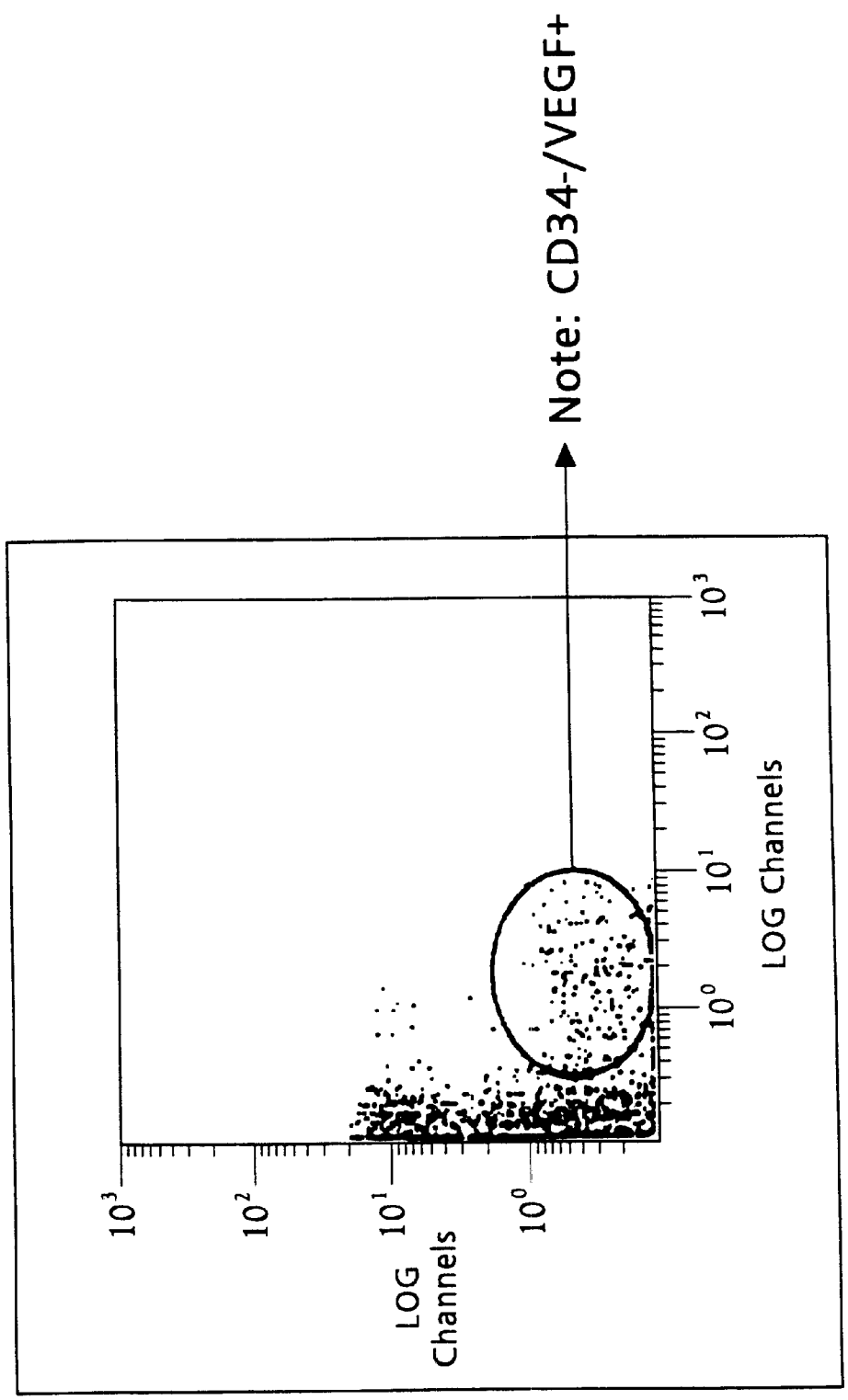
FIG. 7 is a dot plot showing the population profile of initial negatively selected target populations used to inoculated cultures.

FIG. 7 is a dot plot showing the population profile of initial negatively selected target populations used to inoculated cultures. Using CD34 vs. anti-VEGF receptor (VEGFR) we observed the presence of CD34–/VEGFR+ cells in the inocula (see the circled portions of FIG. 7).

Figure 8:
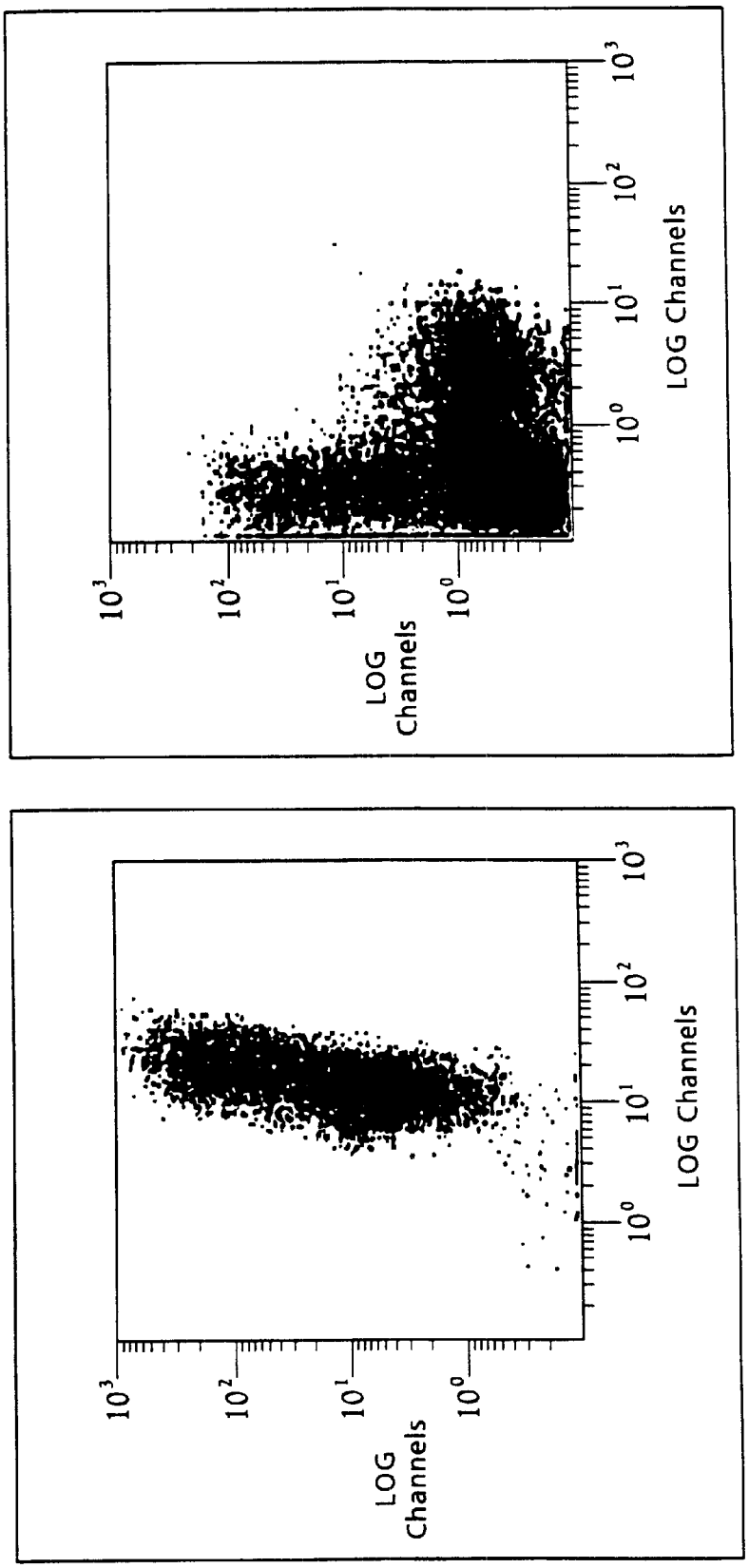
FIG. 8 is a group of dot plots showing the population profile of reselected cells at week three of culture using CD45 vs. MHC I and MHC II and CD34 vs. Flk-1.

FIG. 8 is a group of dot plots showing the population profile of reselected cells at week three of culture using CD45 vs. MHC I and MHC II and CD34 vs. Flk-1. Virtually all cells in this culture are CD45+ and a vast gradient exists in MHC expression. Importantly, the fact that the cells are CD45+ demonstrates that CD34+/–, Flk-1+ cells are not contaminating Human Umbilical Cord Vascular Endothelial Cells (HUVECS), which are CD45–. The gradient in MHC expression demonstrates the presence of both naive and mature leukocytes.

FIG. 9 is a group of dot plots showing the population profile of reselected cells at week three of selective culture using CXCR4 vs. Flk-1 and Pgp (MDR) vs. Flk-1. The circled cells were CD34+ (backgated analysis) and the cells indicated by rectangles were CD34–/CXCR4+/Flk+ and CD34–/Pgp+/Flk+ populations. Notably, CXCR4 is a chemokine receptor responsible for trafficking engrafting cells into the bone marrow. Also, Pgp is the receptor for the Multi-Drug Resistance (MDR) gene product that corresponds to Hoechst Lo, which has been correlated with CD34– cells in the mouse and rhesus that have high engraftment potential.

In combination these observations demonstrate the ex vivo production of clinically relevant numbers of CD34+ and CD34−/CD45+/CD38−/Lin−/Flk+/MDR+/CXCR4+ target cells. This development represents a pivotal contribution to the art, allowing the ex vivo production of rare cells with extraordinary utility in the field of cellular therapeutics.

Other embodiments are within the claims.

What is claimed is:

1. A method for providing a cell population containing non-fetal hemangioblasts, said method comprising
   a) providing a starting sample of cells containing non-fetal hemangioblasts; and
   b) growing cells of said starting sample under conditions that promote the proliferation of said non-fetal hemangioblasts to increase the number of non-fetal hemangioblasts and form the cell population.

2. The method of claim 1 wherein, in step (b), said conditions are such that the number of said non-fetal hemangioblasts and their proximity to each other are sufficient to increase the proportion of non-fetal hemangioblasts in the population, compared to other cells, to provide an enriched cell culture.

3. The method of claim 1 further comprising (c) separating at least a portion of said non-fetal hemangioblasts from other cells in said cell culture.

4. The method of claim 3 wherein said separating step (c) comprises a negative selection process.

5. The method of claim 3 wherein said separating step (c) is performed concurrently with, intermittently during, or following, said growing step (b).

6. The method of claim 3 wherein said separating step is performed more than once during growing step (b).

7. The method of claim 6 wherein said separating step is performed every 5 to 10 days.

8. The method of claim 1 wherein said growing step includes providing at least one growth factor to said cell population during cell proliferation.

9. The method of claim 8 wherein a plurality of growth factors is provided to said cell population.

10. The method of claim 9 wherein said growth factors comprise SCF, TPo and FLT-3.

11. The method of claim 8 wherein said growth factor is VEGF.

12. The method of claim 1 wherein said non-fetal hemangioblasts are human hemangioblasts.

13. The method of claim 1 wherein the non-fetal hemangioblasts provided in the providing step (a) are obtained from human cord blood.

14. The method of claim 12 wherein at least 5% of the non-fetal hemangioblasts are said human hemangioblasts.

15. The method of claim 14 wherein at least 15% of the non-fetal hemangioblasts are said human hemangioblasts.

16. The method of claim 15 wherein at least 25% of the non-fetal hemangioblasts are said human hemangiblasts.

17. The method of claim 12 wherein said human hemangioblasts are characterized as: CD2−, CD3−, CD14−, CD16−, CD19−, CD24−, CD56−, CD66b−, glycophorin A−.

18. The method of claim 17 wherein said human hemangioblasts are further characterized as: flk-1+, CD45+.

19. The method of claim 18 wherein said human hemangioblasts are further characterized as: CXCR4+, MDR+.

20. The method of claim 1 wherein at least some of the non-fetal hemangioblasts are CD 34−, Lin− cells.

21. The method of claim 20 wherein the percentage of cells that are CD 34−, Lin− is higher after the growing step (b) than in the starting cell culture.

22. The method of claim 20 wherein at least 5% of the non-fetal hemangioblasts are said CD 34−, Lin− cells.

23. The method of claim 22 wherein at least 15% of the non-fetal hemangioblasts are said CD 34−, Lin− cells.

24. The method of claim 23 wherein at least 25% of the non-fetal hemangioblasts are said CD 34−, Lin− cells.

25. A method for providing a cell population containing non-fetal uncommitted human hemangioblasts, said method comprising
   a) providing a starting sample of cells containing non-fetal uncommitted human hemangioblasts; and
   b) growing cells of said starting sample under conditions that promote the proliferation of said non-fetal uncommitted human hemangioblasts to increase the number of non-fetal uncommitted human hemangioblasts and form the cell population.

* * * * *